(12) United States Patent
Litvay

(10) Patent No.: US 9,084,700 B2
(45) Date of Patent: Jul. 21, 2015

(54) ABSORBENT ARTICLES HAVING A PULPLESS ABSORBENT CORE WITH IMPROVED PERFORMANCE

(76) Inventor: John D. Litvay, Al Hamra Free Zone (AE)

( * ) Notice: Subject to any disclaimer, the term of this patent is extended or adjusted under 35 U.S.C. 154(b) by 612 days.

(21) Appl. No.: 12/365,408

(22) Filed: Feb. 4, 2009

(65) Prior Publication Data

US 2010/0198178 A1    Aug. 5, 2010

(51) Int. Cl.
| | | |
|---|---|---|
| *A61F 13/15* | (2006.01) | |
| *A61F 13/535* | (2006.01) | |
| *A61F 13/494* | (2006.01) | |
| *A61F 13/53* | (2006.01) | |

(52) U.S. Cl.
CPC ......... *A61F 13/535* (2013.01); *A61F 13/49413* (2013.01); *A61F 13/49453* (2013.01); *A61F 2013/530153* (2013.01); *A61F 2013/530562* (2013.01)

(58) Field of Classification Search
CPC ............ A61F 13/494; A61F 13/49406; A61F 13/49413; A61F 13/49433; A61F 13/49446; A61F 13/49453; A61F 13/475; A61F 13/4751; A61F 13/4755; A61F 2013/4948; A61F 2013/49493
USPC .......................... 604/372, 385.28, 385.19, 365
See application file for complete search history.

(56) References Cited

U.S. PATENT DOCUMENTS

| | | | |
|---|---|---|---|
| 5,462,541 A * | 10/1995 | Bruemmer et al. ........... 604/391 |
| 5,674,215 A * | 10/1997 | Ronnberg ................ 604/385.28 |
| 5,788,684 A * | 8/1998 | Abuto et al. .................. 604/368 |
| 5,868,727 A | 2/1999 | Barr et al. |
| 5,931,826 A * | 8/1999 | Faulks et al. ............. 604/385.27 |
| 6,152,908 A * | 11/2000 | Widlund et al. ......... 604/385.19 |
| 6,632,209 B1 * | 10/2003 | Chmielewski ......... 604/385.101 |
| 6,657,100 B1 * | 12/2003 | Underhill et al. ............. 604/361 |
| 6,703,846 B2 | 3/2004 | Delzer et al. |
| 6,790,202 B2 * | 9/2004 | Klemp et al. ............ 604/385.01 |
| 6,790,798 B1 * | 9/2004 | Suzuki et al. ................ 442/374 |
| 6,962,578 B1 * | 11/2005 | LaVon ..................... 604/385.16 |
| 7,887,527 B2 * | 2/2011 | Hayashi et al. .......... 604/385.28 |
| 7,931,636 B2 * | 4/2011 | LaVon et al. ............. 604/385.28 |
| 8,377,026 B2 * | 2/2013 | Mishima et al. ......... 604/385.28 |
| 2002/0010453 A1 * | 1/2002 | Mishima et al. ......... 604/385.19 |

(Continued)

FOREIGN PATENT DOCUMENTS

WO        0134082 A1    5/2001
WO    WO 2008/018921    2/2008

OTHER PUBLICATIONS

Supplementary European Search Report in PCT/US2010022908, mailed Apr. 9, 2013.

(Continued)

*Primary Examiner* — Lynne Anderson
*Assistant Examiner* — Bradley Philips
(74) *Attorney, Agent, or Firm* — Pillsbury Winthrop Shaw Pittman LLP

(57) ABSTRACT

The embodiments provide an absorbent garment that has an absorbent core that provides for both good leakage and dryness performance. Absorbent garments having a pulpless synthetic core have comparable functionality when compared to more costly absorbent garments having an absorbent core comprising conventional amounts of fluff pulp. The absorbent garments of the embodiments incorporate features that provide good leakage performance and rewet values, while costing considerably less.

21 Claims, 8 Drawing Sheets

(56) References Cited

U.S. PATENT DOCUMENTS

| | | |
|---|---|---|
| 2002/0123733 A1* | 9/2002 | Itoh et al. ............ 604/385.28 |
| 2003/0144644 A1* | 7/2003 | Murai et al. ............ 604/385.27 |
| 2004/0133180 A1 | 7/2004 | Mori et al. |
| 2004/0162536 A1* | 8/2004 | Becker et al. ............ 604/367 |
| 2005/0147711 A1* | 7/2005 | Walter et al. ............ 425/505 |
| 2006/0020250 A1 | 1/2006 | Chester et al. |
| 2006/0040579 A1 | 2/2006 | Sheldon et al. |
| 2006/0167424 A1 | 7/2006 | Chang |
| 2007/0149943 A1* | 6/2007 | Miyamoto ............ 604/385.28 |
| 2007/0191807 A1* | 8/2007 | Hayashi et al. ............ 604/385.28 |
| 2008/0065038 A1 | 3/2008 | Sugiyama et al. |
| 2008/0167634 A1 | 7/2008 | Kouta |
| 2009/0312737 A1* | 12/2009 | LaVon et al. ............ 604/385.26 |

OTHER PUBLICATIONS

Office Action issued on May 5, 2014 in International Application No. EP 10739025.4.

* cited by examiner

Effect of Increasing Curb Height on Core Utilization

ABSORBENT ARTICLES HAVING A PULPLESS ABSORBENT CORE WITH IMPROVED PERFORMANCE

BACKGROUND OF THE INVENTION

1. Field of the Invention

The present invention relates generally to an absorbent article, and more particularly to an absorbent article having a pulpless absorbent core. The absorbent article includes features that provide good leakage performance and rewet values.

2. Description of Related Art

Absorbent products, such as baby diapers, have a 90% to 95% market penetration in the United States and Europe. In contrast, the levels of market penetration in some emerging market countries, such as China and India, are less than 5%. Part of the reason for these low levels of market penetration is the relatively high cost of the absorbent products in those markets. Accordingly, manufacturers of absorbent products in the emerging market countries face an enormous challenge in trying to find ways to produce low cost, but effective, products.

Reducing the amount of raw materials in the absorbent products is one strategy to reduce the overall cost. The cost of raw materials may comprise up to 80% of the total cost in manufacturing the absorbent products. In order to produce a functional product, however, a minimum amount of conventional materials needs to be employed. If a manufacturer reduces the amount of material used beyond such minimum, the functionality of the product may be compromised and the acceptance of the product by consumers could be greatly diminished. For example, it is well known that the most important consumer attributes for baby diapers are leakage control and dryness. Accordingly, reducing the cost of producing baby diapers by reducing raw materials should not compromise the effectiveness of the diapers in controlling leakage and maintaining dryness.

Conventional baby diapers typically are constructed with a moisture-impervious outer backing sheet, a moisture-pervious body contacting inner liner sheet, and a moisture-absorbent core sandwiched between the liner and backing sheet. The absorbent core of these conventional diapers includes fluff pulp and water-absorbing polymers, each serving a different purpose. The fluff pulp in the absorbent cores provides quick absorption of liquids to prevent leakage during an initial insult. Maintaining long term dryness can be accomplished by the slower acting water-absorbing polymers that provide for a more permanent liquid storage and a high absorbency-under-load (AUL). Optimization of these properties may be accomplished by varying amounts and ratios of the pulp and polymer.

Conventional baby diaper cores that contain a fibrous web of fluff pulp and water-absorbing polymers typically maintain adequate polymer efficiency if the core contains less than about 50% water-absorbing polymer. Fluff/polymer diaper cores containing more than 50% water-absorbing polymer generally result in lower polymer efficiency because of gel blocking. Although fluff/polymer cores at greater than 50% polymer can provide adequate absorbency, the overall basis weight of the core typically must be increased to compensate for the lower efficiency of the polymer. Increasing the basis weight decreases the performance/cost ratio of the absorbent core, making them uneconomical. Also, increased basis weights tend to affect the fit and comfort of the garment, as well as impacting the packaging and shipping cost.

Accordingly, there is a need in the art for a cost effective absorbent garment which uses less materials, maintains good leakage performance, and has a long term dryness profile that will provide for a much more comfortable and hygienic product.

The description herein of various advantages and disadvantages of certain elements of known absorbent articles is in no way intended to limit the scope of the invention to the inclusion or exclusion of these elements. Indeed, certain aspects or features of embodiments may include one or more of these elements, without suffering from the disadvantages.

SUMMARY OF THE INVENTION

Certain embodiments of the invention provide an absorbent garment, such as disposable diapers, adult incontinent products, incontinent pads, and sanitary napkins that has an absorbent core that provides for good leakage performance and maintains dryness for improved comfort. It was unexpectedly discovered that absorbent garments having a pulpless synthetic core had comparable functionality as compared to more costly absorbent garments having a fluff pulp core. Such new absorbent garments incorporate important features that can provide good leakage performance and rewet values.

It therefore is a feature of an embodiment of the invention to provide an absorbent article having a pulpless synthetic core. In one embodiment, the absorbent article includes a top sheet, a back sheet, and an absorbent core positioned between the top sheet and back sheet. The absorbent article further comprises a curb having a height that extends from the longitudinal plane of the absorbent core.

In another embodiment, the curb height of the absorbent article provides a pool volume that is at least the same volume as the Centrifuge Retention Capacity (CRC) of the central 60% of the absorbent core. In another embodiment, the absorbent article has a superabsorbent polymer (SAP) absorbency efficiency in the absorbent core that is greater than 95%. In another embodiment, the SAP and synthetic fibers are glued in the absorbent core and the glue is applied using a slot coater. In another embodiment, the absorbent article comprises a transfer layer and the absorbent core is prepared by gluing an amount of SAP such that the width of the glued SAP is less than the width of the transfer layer.

These and other features and advantages of the preferred embodiments will become more readily apparent when the detailed description of the preferred embodiments is read in conjunction with the attached drawings.

DETAILED DESCRIPTION OF PREFERRED EMBODIMENTS

Figure 1:
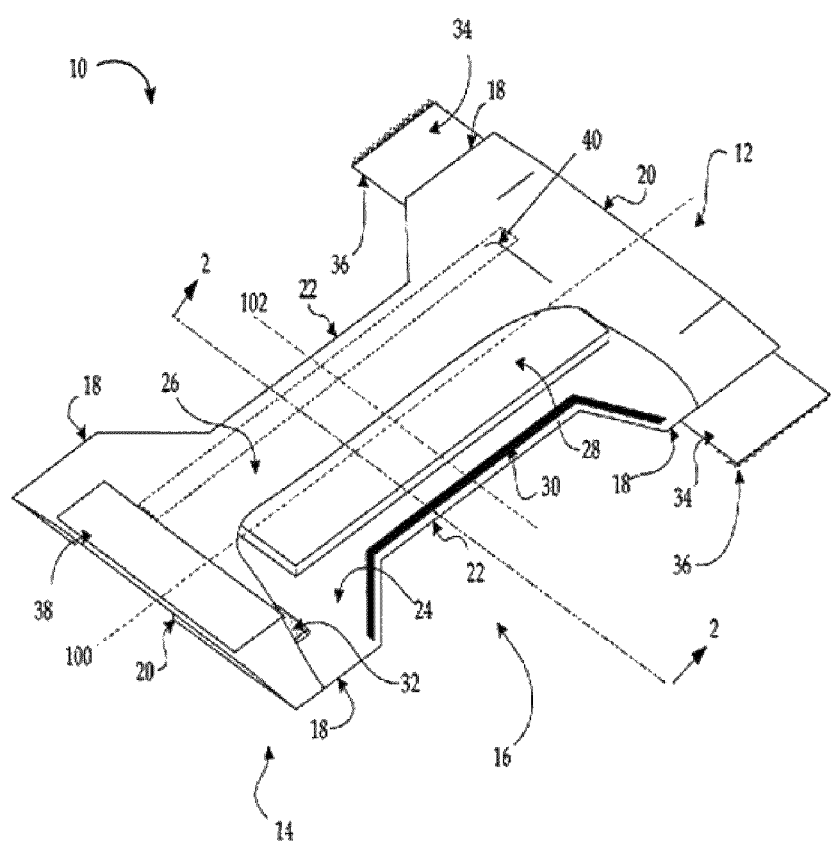
FIG. 1 is a partially cut-away view of a diaper, shown with top sheet facing down and the elastic members fully stretched in the main portion of the garment.

As used herein, the expressions "absorbent garment", "absorbent article", or simply "article" or "garment" refer to devices that absorb and contain body fluids and other body exudates. More specifically, these expressions refer to garments that are placed against or in proximity to the body of a wearer to absorb and contain the various exudates discharged from the body. A non-exhaustive list of examples of absorbent garments or absorbent articles includes diapers, diaper covers, disposable diapers, training pants, feminine hygiene products, and adult incontinence products. Such garments may be intended to be discarded or partially discarded after a single use ("disposable" garments). Such garments may comprise essentially a single inseparable structure ("unitary" garments), or they may comprise replaceable inserts or other interchangeable parts.

The present embodiments may be used with all of the foregoing classes of absorbent garments or absorbent articles, without limitation, whether disposable or otherwise. The embodiments described herein provide, as an exemplary structure, a diaper for an infant, however this is not intended to limit the invention. The invention will be understood to encompass, without limitation, all classes and types of absorbent garments, including those described herein.

Throughout this description, the expressions "upper layer," "lower layer," "above" and "below," which refer to the various components included in the absorbent composite and absorbent core embodiments (including the layers surrounding the absorbent core units) are used merely to describe the spatial relationship between the respective components. The upper layer or component "above" the other component(s) need not always remain vertically above the core or component(s), and the lower layer or component "below" the other component(s) need not always remain vertically below the core or component(s). Indeed, embodiments include various configurations in which the core may be folded in such a manner that the upper layer ultimately becomes the vertically highest and vertically lowest layer at the same time. Other configurations are contemplated within the context of the present embodiments.

The term "component" can refer, but is not limited to, designated selected regions, such as edges, corners, sides or the like; structural members, such as elastic strips, absorbent pads, stretchable layers or panels, layers of material, a transfer layer, a fluid handling layer, or the like; or a graphic.

Throughout this description, the term "disposed" or "positioned," and the expressions "disposed on," "disposed in," "disposed between" and variations thereof (e.g., a description of the article being "disposed" is interposed between the words "disposed" and "on") are intended to mean that one element can be integral with another element, or that one element can be a separate structure bonded to or placed with or placed near another element. Thus, a component that is "disposed on" an element of the absorbent garment can be formed or applied directly or indirectly to a surface of the element, formed or applied between layers of a multiple layer element, formed or applied to a substrate that is placed with or near the element, formed or applied within a layer of the element or another substrate, or other variations or combinations thereof.

Throughout this description, the expressions "top sheet" and "back sheet" denote the relationship of these materials or layers with respect to the absorbent core. It is understood that additional layers may be present between the absorbent core and the top sheet and back sheet, and that additional layers and other materials may be present on the side opposite the absorbent core from either the top sheet or the back sheet.

Throughout this description, the expression "tow fibers" relates in general to any continuous fiber. Tow fibers typically are used in the manufacture of staple fibers, and preferably are comprised of synthetic hygrophobic thermoplastic polymers. Usually, numerous filaments are produced by melt extrusion of the molten polymer through a multi-orifice spinneret during manufacture of staple fibers from synthetic thermoplastic polymers in order that reasonably high productivity may be achieved. The groups of filaments from a plurality of spinnerets typically are combined into a tow which is then subjected to a drawing operation to impart the desired physical properties to the filaments comprising the tow. Tow as used in the context of the present embodiments also encompasses modified tow fibers that have been either surface or internally modified (chemically or otherwise) to improve various desired properties of the fibers (e.g., wicking, etc.).

Throughout this description, the expression "super absorbent polymer" ("SAP") or "super absorbent material" refers to any polymeric material that is capable of absorbing large quantities of fluid by forming a hydrated gel. Super absorbent polymers are well-known to those skilled in the art as substantially water-insoluble, absorbent polymeric compositions that are capable of absorbing large amounts of fluid (e.g., 0.9% solution of NaCl in water, or blood) in relation to their weight and forming a hydrogel upon such absorption. Super absorbent polymers also can retain significant amounts of water under moderate pressures. Super absorbent polymers generally fall into three classes, namely, starch graft copolymers, cross-linked carboxymethylcelluose derivatives, and modified hydrophilic polyacrylates. Examples of such absorbent polymers are hydrolyzed starch-acrylonitrile graft copolymer a neutralized starch-acrylic acid graft copolymer, a saponified acrylic acid ester-vinyl acetate copolymer, a hydrolyzed acrylonitrile copolymer or acrylamide copolymer, a modified cross-linked polyvinyl alcohol, a neutralized self-cross-linking polyacrylic acid, a cross-linked polyacrylate salt, carboxylated cellulose, and a neutralized cross-linked isobutylene-maleic anhydride copolymer.

Throughout this description, the expression "pulpless core" or "pulpless absorbent core," or similar expressions denote an absorbent core having substantially no fluff pulp. Preferably, the absorbent core has less than 5% by weight of the total core of fluff pulp, more preferably, less than 1%, and most preferably, no fluff pulp.

Throughout this description, the expression "curb height" or "curb" denotes an element of the absorbent garment that extends away from the topsheet in a direction orthogonal or at an angle from the longitudinal plane of the absorbent article. That is, if the absorbent article were laid flat on a surface, the curb would extend from the surface. The curb height is the distance the curb extends from the longitudinal plane of the absorbent core. In a preferred embodiment, the curb is formed as an extension of, or integral with the leg elastics.

The present embodiments relate generally to absorbent articles, and in particular to absorbent articles that contain a top sheet, a back sheet, and an absorbent core positioned at least partially between the top sheet and the back sheet. The absorbent core of the embodiments include synthetic fibers and super absorbent polymers (SAP), but preferably do not contain fluff pulp.

The embodiments are premised in part on the discovery that absorbent garments of the present invention having a pulpless synthetic core can have superior functionality when compared to more costly absorbent garments having fluff pulp matrix cores. In contrast to traditional absorbent garments having a core comprising fluff pulp and water-absorbing polymers, embodiments of the present invention incorporate important design features into a pulpless absorbent core to yield good leakage performance and rewet values.

The embodiments now will be described with reference to the attached drawings illustrating preferred embodiments. Some of the features that appear in more than one Figure have the same reference number in each Figure.

FIG. 1 is a partially cut away depiction of an exemplary embodiment of an absorbent garment 10 (preferably a disposable absorbent garment). The embodiment shown in FIG. 1 is an infant's diaper. This depiction, however, is not intended to limit the invention, and those skilled in the art appreciate that the invention covers other types of absorbent articles. For simplicity, the preferred embodiments will be described with reference to an infant's diaper. The garment 10 of FIG. 1 is depicted in a generally flattened position, with the body-facing side facing down, and with the various elastic components depicted in their relaxed condition with the effects of the elastics removed for clarity (when relaxed, the elastics typically cause the surrounding material to gather or "shirr"). In the flattened position, the garment 10 may have a generally hourglass shaped structure, but it may also have any other shape suitable for the given application, such as a rectangular shape, a trapezoidal shape, a "T" shape, and the like.

As used herein, the longitudinal axis 100 of the garment is the dimension of the garment corresponding to the front-to-rear dimension of the user, and the lateral (or transverse) axis 102 of the garment is the dimension corresponding to the side-to-side dimension of the user. The longitudinal axis 100 and the transverse axis 102 make up the longitudinal plane of the garment.

In use, the embodiments comprise a garment 10 having a pant-like configuration with a waist-encircling region and a crotch region. The waist-encircling region may comprise a first waist region 12, disposed adjacent to, for example, the back waist region of a wearer's body, and a second waist region 14, disposed adjacent to, for example, the front waist region of a wearer's body, when the garment is worn. The first and second waist regions 12, 14, may correspond to the front and back of the wearer's body, respectively, depending on whether garment 10 is attached in front of or behind the subject wearer. The first and second waist regions may be joined together at or near their lateral edges 18, causing the longitudinally distal edges 20 of the garment 10 to form the perimeter of a waist opening. A crotch region 16 extends between the first and second waist regions, 12, 14, and the crotch edges 22 form the perimeter of a pair of leg openings, when the garment 10 is placed on a subject wearer.

The garment preferably comprises a top sheet 24, and a back sheet 26. When the garment 10 is being worn, the top sheet 24 faces the wearer's body, and the back sheet 26 faces away from the wearer. An absorbent core 28 preferably is positioned between at least a portion of the top sheet 24 and the back sheet 26.

A feature of an embodiment may further comprise various additional features. One or more pairs of elastic gathers 30 (leg elastics) may extend adjacent the crotch edges 22. The garment 10 also may comprise one or more waste containment systems, such as inboard standing leg gathers 40, which preferably extend form the second waist region 14 to the first waist region 12 along opposite sides of longitudinal center line 100 (only one standing leg gather system 40 is shown in FIG. 1 for purposes of clarity). One or both of the first and second waist regions 12, 14 may also be equipped with strips of waist elastic material 32, such as elastic waist foam or other elastically extensible material, which help contract the garment around the wearer's waist, providing improved fit and leakage prevention. In addition, the ear portions of the garment, e.g., those portions immediately adjacent lateral edges 18 and extending to crotch edges 22, can be comprised entirely or only partially of elastically extensible material (not shown).

The absorbent garment 10 also preferably includes fastening elements to enable attachment of the first waist region 12 to second waist region 14. Fastening elements preferably include a pair of tabs 34 that extend laterally away from opposite lateral edges 18 of the first waist region 12 of the garment 10. The tabs 34 may comprise in whole or in part an elastically extensible material (not shown), and may be designed to stretch around a wearer's waist to provide improved fit, comfort, and leakage protection. Such tabs 34 may be used in conjunction with, or in lieu of, waist elastic material 32, such as foam, or other elastically extensible materials.

At least one fastening mechanism 36 (collectively referred to as "fastener 36") is attached to each tab 34 for attaching the tab to the second waist region 14, thereby providing the garment 10 with a pant-like shape, and enabling garment 10 to be fixed or otherwise fitted on the wearer. The fasteners 36 may attach to one or more target devices 38 located in the second waist region 14. For example, in one embodiment, the fastening mechanism is a hook and loop fastener, where one fastening element is a hook portion, and a corresponding target device is a loop portion of the hook and loop fastener, or the target device may be the backsheet itself. In another embodiment, the fastening mechanism is a tape fastener system, where one fastening element is an adhesive tape, and a corresponding target device is a tape receiving surface. Other fastening systems may be used in this invention, as long as they are capable of fastening the garment 10 about the wearer.

Although not shown in the drawings, the absorbent garment 10 may also include grips attached along the distal edges of each tab 34 to enable a caregiver to pull the grips, and not on the ends of the tabs 34, around the wearer and over the target devices 38 to thereby secure the fasteners 36 to the one or more target devices 38.

The various parts of the garment 10 can be attached to one another or associated with one another to form a structure that preferably maintains its shape during the useful life of the garment 10. As used herein, the terms "attached", "joined", "associated", and similar terms encompass configurations in which a first part is directly joined to a second part by affixing the first part directly to the second part, by indirectly joining the first part to the second part through intermediate members, by fixing the relative positions of various parts by capturing parts between other parts, or by integrally forming the first and second parts. Those skilled in the art will appreciate that various methods or combinations of methods may be used to securely join, attach, or otherwise associate the respective parts of the garment 10 to one another.

The top sheet 24 and back sheet 26 may be constructed from a wide variety of materials known in the art. The embodiments are not intended to be limited to any specific materials for these components. The back sheet 26 preferably is made from any suitable pliable liquid-impervious material known in the art. Typical back sheet materials include films of polyethylene, polypropylene, polyester, nylon, and polyvinyl chloride and blends of these materials. For example, the back sheet can be made of a polyethylene film having a thickness in the range of 0.02-0.04 mm. The back sheet 26 may be pigmented with, for example, titanium dioxide, to provide the garment 10 with a pleasing color or to render the back sheet 26 opaque enough that exudates being contained by the garment 10 are not visible from outside the garment. In addition, the back sheet 26 may be formed in such a manner that it is opaque, for example, by using various inert components in the polymeric film and then biaxially stretching the film. Other back sheet materials will be readily apparent to those skilled in the art. The back sheet 26 preferably has sufficient liquid imperviousness to prevent any leakage of fluids. The required level of liquid imperviousness may vary between different locations on the garment 10. The back sheet 26 may be covered with a fibrous, non woven fabric such as is disclosed, for example, in U.S. Pat. No. 4,646,362 issued to Heran et al., the disclosure of which is hereby incorporated by reference in its entirety.

The moisture-pervious top sheet 24 can be comprised of any suitable relatively liquid-pervious material known in the art that permits passage of liquid there through. Non-woven liner sheet materials are exemplary because such materials readily allow the passage of liquids to the underlying absorbent core 28. Examples of suitable liner sheet material include non-woven spun bond or carded webs of polypropylene, polyethylene, nylon, polyester, and blends of these materials.

The top sheet 24 and back sheet 26 can be shaped and sized according to the requirements of each of the various types of absorbent garments, or to accommodate various user-sizes. In an embodiment in which the garment 10 is a diaper or an adult incontinence brief, the combination of top sheet 24 and back sheet 26, may have an hourglass shape, as seen in FIG. 1, or may have a rectangular, trapezoidal, "T" shape, or other shape.

The underlying structure beneath the top sheet 24 may include, depending on the diaper construction, various combinations of elements, but in each embodiment, it is contemplated that the absorbent garment will preferably include an absorbent core 28 comprising synthetic fibers and SAP. In addition, an additional layer 29 may be disposed between the top sheet 24 and absorbent core 28, and/or other additional layer(s) 29 may be disposed between these layers, or between absorbent core 28 and back sheet 26. The additional layer(s) 29 may include a fluid transfer layer, a fluid handling layer, a storage layer, a wicking layer, a fluid distribution layer, and any other layer(s) known to those having ordinary skill in the art.

Although the absorbent core 28 depicted in FIG. 1 has a substantially rectangular cross-sectional and plan view shape, other shapes may be used, such as a "T" shape or an hourglass shape. The shape of the absorbent core 28 may be selected to provide the greatest absorbency with a limited amount of material. The absorbent core may be associated with the top sheet 24, back sheet 26, or any other suitable part of the garment 10 by any method known in the art, in order to fix the absorbent core 28 in place. Persons of ordinary skill in the art are capable of designing and wrapping a suitable absorbent core 28 of the embodiments, using the guidelines provided herein.

Figure 2:
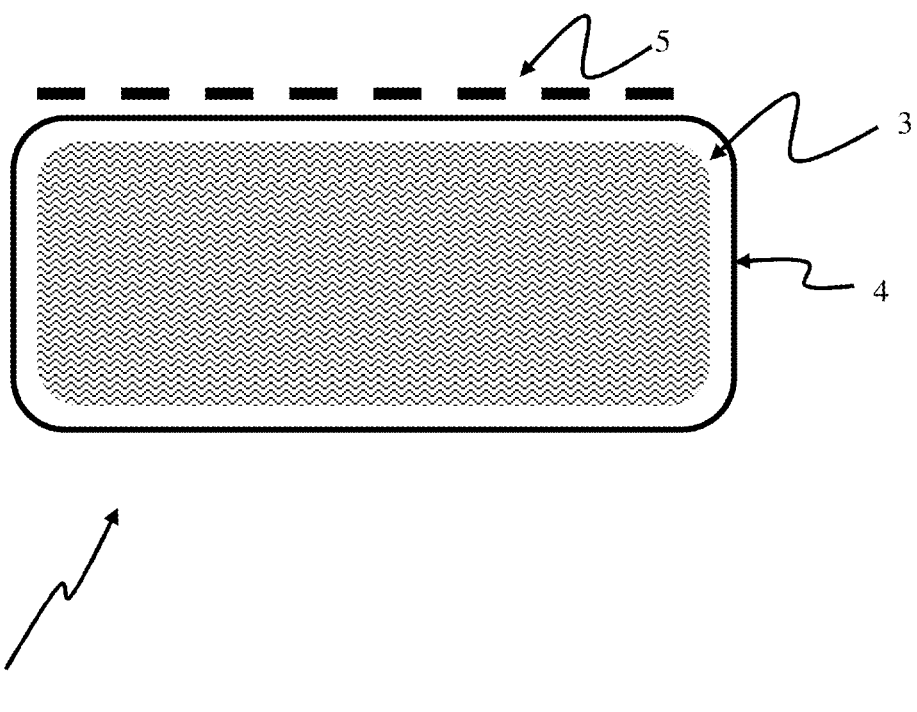
FIG. 2 is a cross-sectional view of an absorbent core according to one embodiment showing synthetic fibers.

FIG. 2 is a cross-sectional view of absorbent core 28. In addition to the respective layers in the absorbent core 28, the overall absorbent core 28 may be enclosed within a tissue wrapping 4, such as is disclosed, for example, in U.S. Pat. No. 6,068,620, the disclosure of which is incorporated by reference herein in its entirety. The liquid pervious tissue overwrap, or other material may be treated to be hydrophobic or hydrophilic, or to have other properties. The wrap 4 can be a cellulosic tissue or synthetic non-woven made from any polyolefin which is hydrophilic. The use of a cellulosic wrap does not mean that the core could be classified as a fluff-containing product. Indeed, the core portion will contain no fluff, even if the wrap 4 is comprised of a cellulosic tissue. Also shown in FIG. 2 is fiber matrix 3 and acquisition or transfer layer 5. The absorbent core 28, and any (tissue) wrap enclosing it, may be folded, crimped, thermally bonded, or sonic bonded, or otherwise manipulated to provide additional benefits. It is envisioned that a variety of folding patterns may be employed to provide additional fluid handling capabilities. For example, absorbent core 28 may be folded into a U shape, a C shape, a G shape, a Z shape, or other shapes, as viewed along the longitudinal axis 100, to provide fluid handling channels, multiple layers of absorbent material, or other benefits.

The fiber matrix 3 may be made from any synthetic material known in the art that can be made into tow fibers. Such materials include synthetic materials such as polyolefins, rayon, polycarbonates and cellulose acetate. Polyolefins include polypropylene, polyethylene, and any recycled plastics that have the appropriate properties to be made into tow. The synthetic materials may also include colorants and the adherence of diagnostic chemicals to the fiber surfaces.

The feeding system disclosed in U.S. Pat. No. 6,923,926, the disclosure of which is incorporated herein by reference in its entirety with the present invention, may be used to manufacture the absorbent core. It also is understood that the manufacture of the absorbent core can be completed off line of the manufacturing of the rest of the absorbent garment components. It is possible for example for one forming unit to supply several diaper manufacturing machines.

Figure 3:
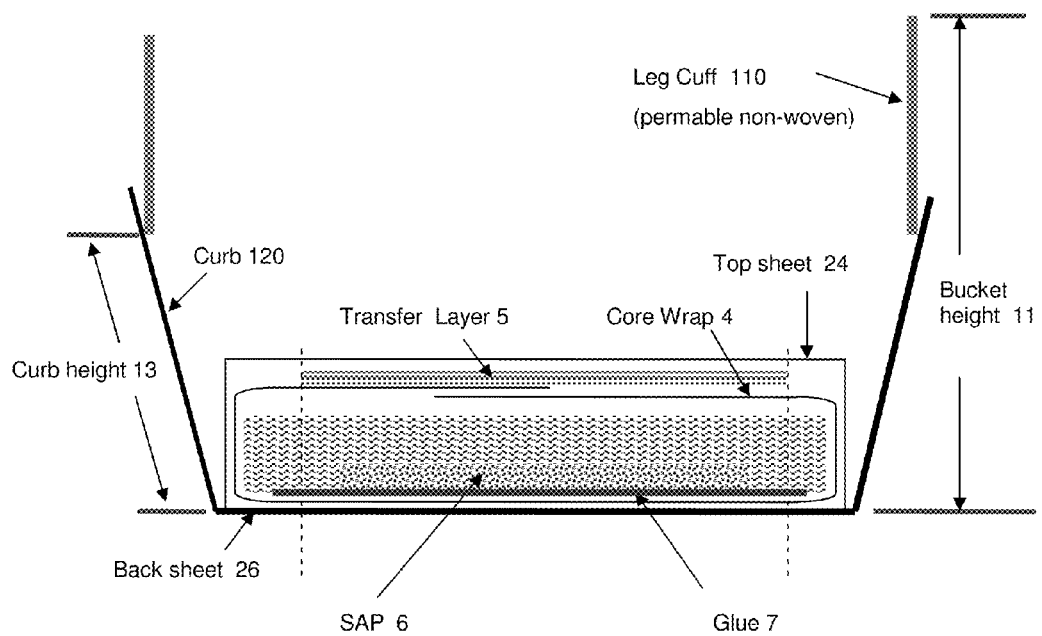
FIG. 3 is a cross-sectional view of an absorbent garment according to one embodiment.

Turning now to FIG. 3, a cross-section of a first embodiment of a pulpless diaper 10 is shown. Diaper 10 includes an absorbent core disposed between top sheet 24 and bottom sheet 26. Diaper 10 further includes curb 120 and leg cuff 110. Curb 120 preferably can be formed by the portion of the backsheet that lies between the core and the bottom of leg cuff 110 while the diaper is under tension and in the normal or "in use" position. Curb height can be calculated by measuring the distance from the bottom of the core to the bottom of leg cuff 110. Curb height preferably is measured at the front end or back end of the diaper.

As discussed previously, a standard pulp diaper minimizes liquid urine leakage by having a core comprised of fluff pulp that absorbs or traps liquid quickly, while allowing moisture absorbing polymers to gradually lock the urine up against pressure. For a pulpless diaper the mechanisms that can be used to reduce leakage are different due to the fact that the fluff pulp component is missing. Hence the ability to control a short term surge should be compensated in order to achieve the performance levels found in conventional pulp diapers. While not intending on being bound by any theory of operation, the present inventor has found that one factor useful in attaining good urine leakage performance levels in pulpless diapers is the creation of a curb that helps define the dimensions to create a pool volume having an appropriate capacity to hold or store urine until the SAP can completely absorb the urine. It is understood that leakage pertains to both urine and bowel movements. However, most studies and research have been directed at controlling urine leakage since urine leakage is the most prevalent leakage category. Accordingly, leakage will be referred to as pertaining to liquid urine leakage.

Curb 120, which preferably is comprised of an impermeable plastic film formed from the backsheet, (either formed as a separate material and joined to the backsheet, or formed integrally with the backsheet) forms a pool volume when the diaper is under tension, as is usually the case when in use. The pool volume is dependant on curb height. The pool volume allows the diaper to retain urine or other liquids so that SAP 6 in the absorbent core can absorb the urine. Pool volume may be calculated using following equations:

Pool volume (mm³)=core width (mm)×curb height (mm)×core length used (mm)   Equation 1

Pool volume (mm³)=core width (mm)×0.5 (length between the leg cuffs−core width) (mm)×core length used (mm)   Equation 2

Pool volume differs from the bucket volume found in traditional fluff pulp diapers. Bucket height preferably can be calculated by measuring the distance from the bottom of the core to the top of leg cuff 110 while the diaper is under tension in the normal or "in use" position. Bucket volume may be calculated with the following equations:

Bucket Volume (mm³)=core width (mm)×bucket height (mm)×core length used (mm)   Equation 3

Bucket Volume (mm³)=core width (mm)×(curb height+leg cuff height) (mm)×core length used (mm)   Equation 4

Bucket volume is not an effective indicator in the leakage performance of a pulpless diaper. Leg cuff 110 is normally a hydrophobic non-woven attached to either the backsheet or directly onto the core. Liquid can seep out of the leg cuff prior to SAP 6 absorbing all the liquid especially if the swollen core touches the leg cuff. Accordingly, it is important to have a curb height that will create the necessary volumetric capacity or pool volume to retain all the liquid while the SAP 6 absorbs the liquid. The curb height is preferably greater than 6 mm, more preferably greater than 10 mm, and most preferably greater than 15 mm.

Figure 4:
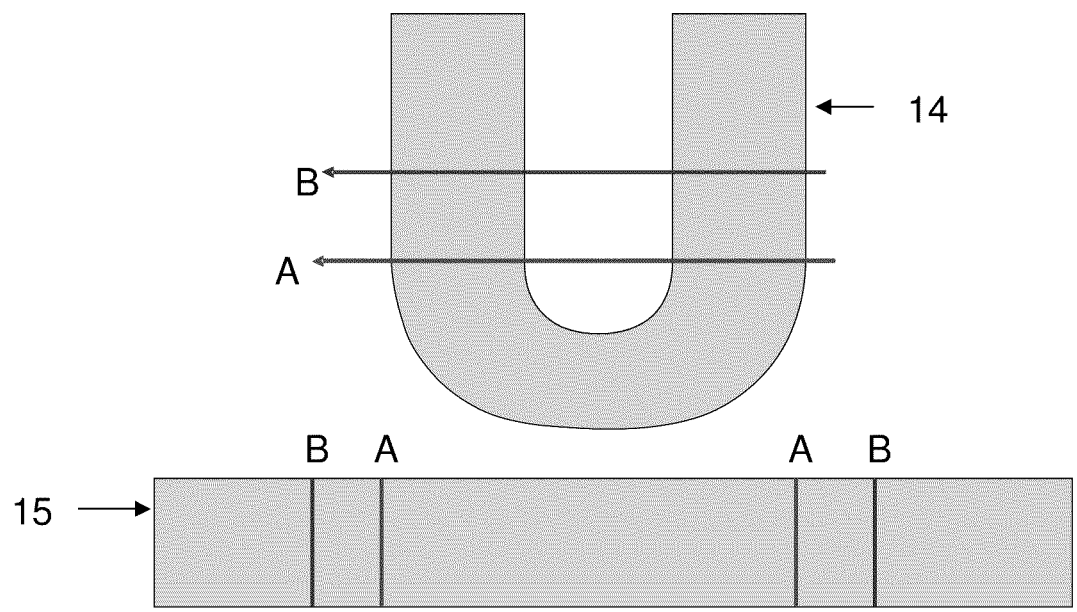
FIG. 4 illustrates the concept of increasing pool volume and core utilization by increasing the curb height.

FIG. 4 illustrates one effect of increasing curb height on the pool volume. By increasing curb height in a diaper, the amount of hydrohead core utilization likewise increases. The increase in curb height plus the increase in core length utilization increases the pool volume, as shown by equation 1. FIG. 4 shows a longitudinal section 14 through a diaper while in the U-shape or normal in use position. Two curb height positions designated position A and position B are shown. As the curb height is increased from position A to position B, the used core length increases and thus the core utilization increases. A planar view of the flat stretched out core 15 having positions A and B denoted shows that the core length used increases as the curb height is increased from position A to position B.

Table 1 shows the effect of core length utilization, core width, and curb height on the pool volume. The calculations in table 1 are premised on the use of a size 4 or large diaper which typically has a 380 mm core length and that 60% of the core length is utilized.

TABLE 1

Pool Volume Calculations Using Equations 1 and 2

| Set | Core Length Utilized (mm) | Length Between Leg Cuffs (mm) | Core Width (mm) | Curb Height (mm) | Pool Volume (cc) |
|---|---|---|---|---|---|
| 1 | 228 | 130 | 120 | 5 | 137 |
| 2 | 228 | 139 | 120 | 9.5 | 259 |
| 3 | 228 | 142 | 120 | 11 | 300 |
| 4 | 228 | 142 | 117 | 12.5 | 333 |

Preferably, the appropriate pool volume that is required to optimize protection and performance should be equal to or greater than the Centrifuge Retention Capacity (CRC) of the utilized portion of the core ("pool CRC"). The total CRC of a core and the pool CRC may be calculated by the following equations:

CRC of core (grams)=total SAP in core (grams)×expected SAP CRC (grams/grams)   Equation 5

Pool CRC (grams)=CRC of core (grams)×utilization of core (%)   Equation 6

Table 2 shows the CRC of a core and the pool CRC of exemplary absorbent cores relative to the total SAP contained in the core and the expected CRC of the SAP. Pool CRC is based on a utilization of 60% of the total core length.

TABLE 2

Pool CRC Calculations

| Set | Total SAP in core (grams) | Expected CRC of SAP (grams liquid/grams SAP) | CRC of core (grams of liquid) | Pool CRC (grams of liquid) |
|---|---|---|---|---|
| 1 | 13 | 31 | 403 | 241 |
| 2 | 13 | 36 | 468 | 280 |
| 3 | 13.5 | 31 | 419 | 251 |
| 4 | 13.5 | 36 | 486 | 292 |
| 5 | 14.0 | 31 | 450 | 270 |
| 6 | 14.0 | 36 | 504 | 302 |
| 7 | 14.5 | 31 | 450 | 270 |
| 8 | 14.5 | 36 | 522 | 313 |

In another embodiment of the invention, the absorbent garment has a high SAP absorbency efficiency as calculated using the Centrifuge Retention Capacity (CRC) of the diaper as compared to the expected CRC of the SAP contained in the diaper. Centrifuge Retention Capacity of a diaper preferably is calculated according to the following protocol. The dry weight of a representative diaper is recorded. Next the diaper is submersed into a 1% saline solution for 30 minutes. The diaper then is removed and placed into a Thomas 772 SEK 287 centrifuge and spun for two minutes. After centrifuging, the diaper is removed and reweighed to yield the wet weight. Using the dry weight and wet weight, two CRC numbers corresponding to the CRC of the diaper and the CRC of the SAP are calculated. The following equations show the formula for calculating these numbers.

CRC of Diaper (grams)=wet weight (grams)−dry weight (grams)   Equation 7

CRC of SAP (gram/gram)=CRC of Diaper (gram)/weight of SAP in diaper (gram)   Equation 8

Weight of SAP in diaper (gram)=SAP target weight (gram)+(dry weight of the diaper−diaper target weight) (gram),   Equation 9 where target weight is the weight that the diaper should be as fabricated, and consequently, the target weight of a diaper will indicate a certain amount of SAP included in the diaper.

Figure 5:
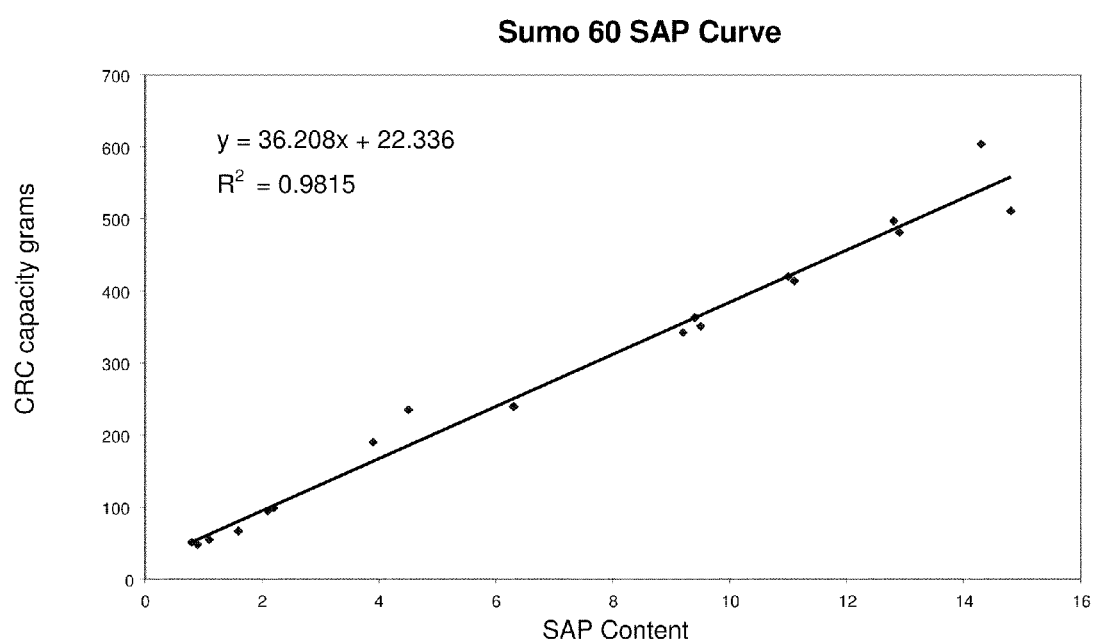
FIG. 5 is a graph showing the CRC absorption of a super absorbent polymer (SAP) within a pulpless diaper according to one embodiment.

FIG. 5 illustrates the SAP absorbency efficiency of an exemplary absorbent garment. The Centrifuge Retention Capacity (CRC) of a pulpless diaper having a core containing SUMITOMO 60 II SX SAP was compared to the actual grams of SUMITOMO 60 II SX SAP contained in the pulpless diaper core using a 1% synthetic urine. SUMITOMO 60 II SX SAP, or SA60SXII, is a superabsorbent particle having a retention absorbency of about 41 g/g, an absorption capacity of about 58 g/g, a bulk density of about 0.69 g/ml, and is commercially available from Sumitomo Seika Singapore PTE. Ltd., Singapore. FIG. 5 illustrates the highly linear nature of the absorbency of the synthetic core and the slope of the line, which for this particular embodiment, is about 36.208. The slope is the gram/gram absorbency of the SAP while in the diaper. The CRC specification for SUMOTOMO 60 II SX sap is 36 grams/gram. Therefore, the synthetic core diaper has a SAP absorbency efficiency of 100%. Due to the absorption and subsequent release of water by fluff during CRC testing, standard fluff containing diapers have a SAP absorbency efficiency typically below 90%.

In another embodiment of the invention, the glue used to secure the SAP is applied using a slot coater. Two primary conditions exist that result in urine leakage: (1) free urine; and (2) a means of escape. Accordingly, another element useful in obtaining proper containment of the urine is the X-Y SAP distribution in the pulpless core. Specifically the type of application of glue onto the core wrap may help to dictate the distribution, and therefore can influence the leakage performance of the resulting diaper. More specifically, spray applications of glue may lead to lower coverage percentage and a channeled pattern that can potentially lead to premature containment failure of the diaper and lower leakage performance.

Figure 6:
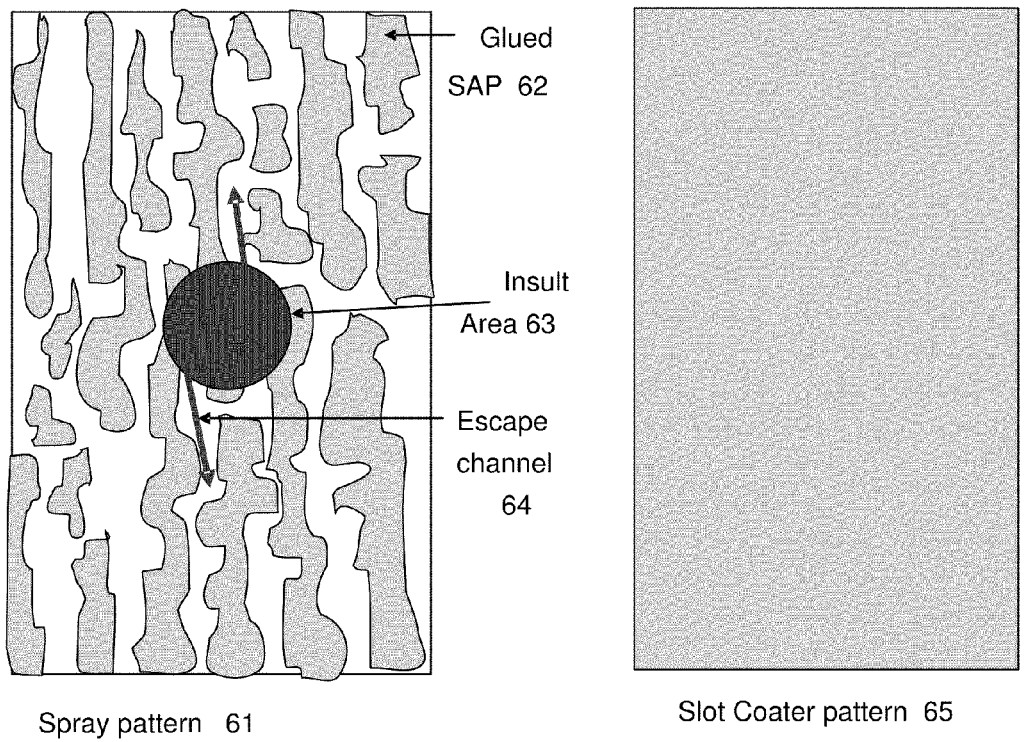
FIG. 6 illustrates the glue/SAP patterns obtained by spraying or slot coating of the core wrap.

FIG. 6 illustrates the glue patterns that are obtained, and consequently the SAP pattern, when glue is applied to the core wrap using a spray device and a slot coater. Spray pattern 61 shows the glue pattern obtained by spraying glue on a cellulosic or non-woven core wrap. The SAP pattern 62 mirrors the glue pattern since the SAP adheres to and is bonded to the glue. The resulting pattern when using a spray device is a discontinuous pattern of MD oriented or aligned strands or islands. Between these islands are channels that contain no glue or SAP and therefore are avenues for escape of the urine once the diaper is insulted.

When liquid such as urine strikes an insult area 63 of the core, the liquid may begin to spread throughout the core via channels 64 formed by the glue pattern. The channels 64 preferably are non-SAP containing and form an avenue of escape that the liquid can travel down in the MD direction of the diaper. The urine therefore can ultimately escape from the diaper in the area of the waist. The MD oriented channels preferably are caused by the MD direction flow of the diaper during its production, and subsequent application of glue.

In contrast, slot coated application of glue results in essentially 100% coverage and an improved barrier to urine escape. Slot coater pattern 65 shows the complete glue and SAP coverage when glue is applied with a slot coater.

Figure 7:
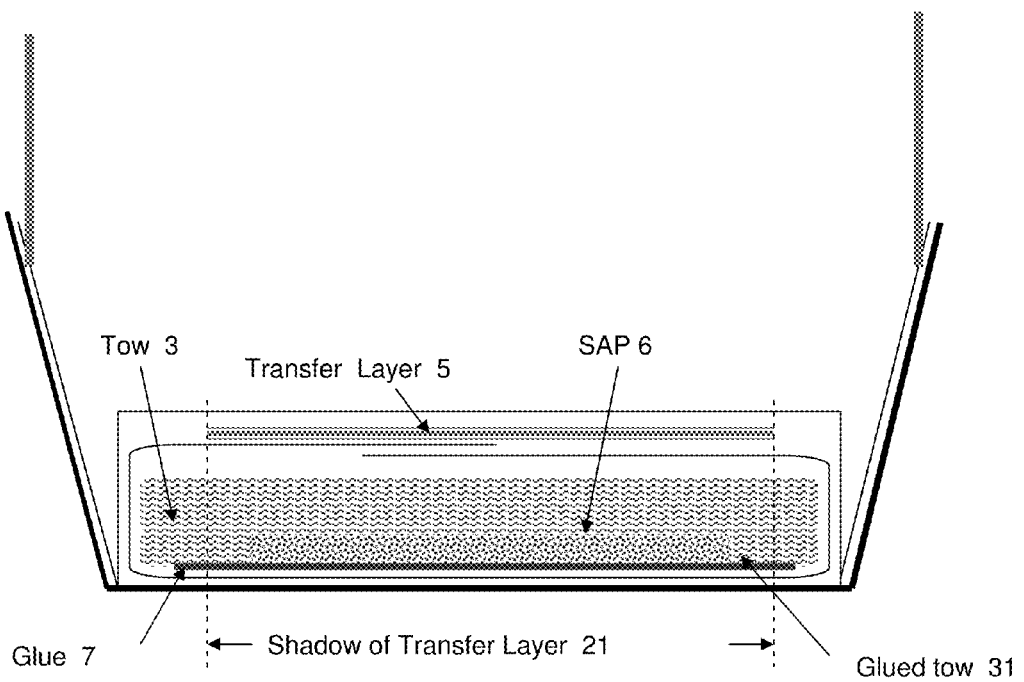
FIG. 7 is a cross-sectional view of an absorbent garment according to one embodiment illustrating the containment of the SAP within the "shadow of the transfer layer"

Turning now to FIG. 7, a cross-sectional view of an embodiment of an absorbent garment is shown where the SAP 6 is glued to the wrap such that the SAP 6 is contained under or within the shadow of the transfer layer 21. While not intending on being bound by any theory of operation, the inventor believes that maintaining the SAP 6 within the lateral boundaries of the shadow of the transfer layer 21 improves the rewet performance and hence the dryness of the diaper.

In order to maintain the SAP within the lateral boundaries of the shadow of the transfer layer the following criteria preferably are met. The SAP delivery system should deliver SAP within a narrower width than that of the transfer layer. The distributed SAP must be contained and not be allowed to shift or spread in the CD direction of the diaper. To accomplish this the glue that is applied preferably has a width that is wider than the SAP width and permits the tow to be bonded to the glue while encapsulating and sealing the SAP. The result is a well defined absorbent core geometry with the co-comittment absorption zone. Thus, these relative application widths and dimensions preferably are controlled in order to achieve the desired results. By containing the SAP within the lateral boundaries of the shadow of the transfer layer 21 and gluing tow in a width wider than the SAP application width, the glued tow 31 contains the SAP, does not allow the SAP to migrate or shift, thereby maintaining maximum absorbency under the transfer layer and lowering the rewet values and obtaining a dryer diaper. Those skilled in the art will be capable of controlling the relative application widths and dimensions using the guidelines provided herein.

Embodiments of the invention now will be explained with reference to the following non-limiting examples.

Example 1

Consumer Panel Testing for Leakage Performance

Table 3 below shows the values obtained from Panel testing three different diaper variants. The panel tests were conducted in Holland and employed approximately 60 families. The score for "It leaks" is the consumers' assessment of the leakage performance of the diaper. A score of 26.8% means that 26.8% of the approximate 60 families had diapers that leaked during the study.

TABLE 3

| | Panel Tests | | | |
|---|---|---|---|---|
| | Question | 1st Panel | 2nd Panel | 3rd Panel |
| Diaper Design | It Leaks | 26.8 | 24.1 | 17.9 |
| Pool CRC (grams) - 60% core utilization | | 241 | 241 | 313 |
| Pool Volume (cc) | | 137 | 259 | 333 |
| Bucket Volume (cc) | | 1300 | 1240 | 1400 |

Panel data was collected from 60 families by B&N Panel Wizard Post Bus 94209 1090 GE Amsterdam Comparing the scores of panel 1 and panel 2 in table 3, the traditional bucket volume does not appear to correlate with improved urine leakage in pulpless diapers. The higher bucket volume in panel 1 as compared to panel 2 did not result in better performance, but rather in worse performance.

One reason for this effect is believed to be due to calculating the bucket volume using the height of the leg cuff. Leg cuffs are traditionally made from a hydrophobic non-woven, however, which can allow leakage once they are wetted. Another way to increase pool volume besides increasing the curb height is to replace the non-woven leg cuff material with a more permanent barrier thus achieving a similar effect as increasing curb height.

In addition, it is well know that one technique employed to improve leakage is to increase the core capacity. As shown by panel 1, however, a diaper may have a high core capacity but this potential performance is not realized due to the limitations on leakage performance imposed by the diaper design, namely the curb design and its pool volume.

Thus, a balanced diaper design should have a pool volume that is equal to or greater than pool CRC in order to achieve optimal performance. A comparison of the scores from panel 2 and 3 reveals that leakage is reduced when both pool CRC and pool volume is increased.

As can be seen from some of the data of Table 3, the core can be overdesigned, i.e. increase cost without improved leakage performance. As shown in the results of panel 1 and 2, an increase in the pool volume resulted in a substantial decrease in the number of consumers that experienced leakage. This points directly to the importance of the curb and its corresponding pool volume being a relatively important factor in obtaining good pulpless diaper performance.

A parameter that is believed to affect leakage performance therefore is curb height in that this parameter affects both "pool volume" and the amount of SAP or core efficiency that can be obtained. As shown in FIG. 4, when curb height is increased from Position A to Position B the pool volume increases due to the height value increasing in addition to the increased core utilization.

To improve overall leakage performance it is preferable to have a balanced design of the core capacity and the curb volume so the full potential of the diaper design can be realized. The present inventor believes that increasing the core capacity will only improve leakage performance if the pool volume also is increased proportionally.

Example 2

Leakage Performance From Different Glue Application

As discussed previously, another element that can enhance the performance of the absorbent garment is the method of applying glue to the absorbent core. FIG. 6 illustrates two patterns made from two application processes. From this illustration it can be seen that the incomplete coverage and channeling pattern of the spray pattern can lead to urine escape. This figure also shows the more complete coverage of a slot coating pattern. This also is shown in Table 4 below which contains the simulated leakage values obtained by diapers that have been constructed using both the spray and slot coating glue application methodologies as tested at the Courtray laboratories in France (2 Rue Charles Monsaart, 59500 Douai, France). The number for each diaper represents the number of milliliters of synthetic urine the diaper absorbed before it leaked. Therefore the higher the number the better the leakage performance.

TABLE 4

Glue Applicator Data

| | Set 1 ml | Set 2 ml | Set 3 ml | Set 4 ml | Set 5 ml | Set 6 ml | Set 7 ml | Set 8 ml |
|---|---|---|---|---|---|---|---|---|
| Applicator | Spray | Spray | Spray | Spray | Slot | Slot | Slot | Slot |
| Rep 1 | 289 | 248 | 340 | 338 | 352 | 346 | 293 | 318 |
| Rep 2 | 327 | 244 | 219 | 337 | 350 | 330 | 343 | 342 |
| Rep 3 | 176 | 177 | 299 | 345 | 348 | 355 | 335 | 347 |
| Rep 4 | 335 | 237 | 296 | 312 | 350 | 354 | 340 | 351 |
| Rep 5 | 250 | 248 | 287 | 353 | 355 | 3556 | 338 | 351 |
| Rep 6 | 355 | 249 | 333 | 358 | 353 | 348 | 343 | 352 |
| Rep 7 | 354 | 249 | 290 | 343 | 349 | 351 | 342 | 353 |
| Rep 8 | 311 | 249 | 327 | 314 | 353 | 358 | 337 | 358 |
| Ave | 300 | 238 | 299 | 338 | 351 | 350 | 334 | 347 |
| Std Dev | 61.0 | 24.8 | 38.3 | 16.7 | 2.4 | 9.0 | 16.8 | 12.4 |

An examination of Table 4 shows that the diapers manufactured using the spray method have a higher standard deviation than the diapers manufactured using the slot coating method and therefore may leak prematurely. In addition, the average number of milliliters of synthetic urine absorbed was higher in the slot coated set of samples, indicating better leakage performance.

Example 3

Test for Rewet Performance

Another important attribute of a diaper is dryness. There are many ways that consumers assess dryness. For a consumer, the dryness of a baby's skin after wearing the diaper all night can be an important test of a diaper's performance for both leakage and dryness. For the researcher and diaper manufacture there has been developed numerous methods to assess diaper dryness. One such test to measure the dryness of a diaper is a rewet test.

The general rewet tests use a protocol similar to the following: The diaper is opened and then insulted with a measured amount of synthetic urine. After insult, the diaper is left to hydrate for a specific time period, usually 5-20 minutes. After the hydration time, a pre-weighed blotter of some type is laid on top of the insult area and the diaper is blotted for a specified time period under a specified pressure or load. The now wet blotter is removed from the diaper and reweighed. Using the two weights, the amount of synthetic urine transferred to the blotter paper can be calculated. This weight of blotter transferred urine is the measure of a diapers dryness, i.e. the less synthetic urine transferred from the diaper, the drier the diaper. This procedure of insulting the diaper with synthetic urine is usually repeated on the same diaper, with three insults being the norm.

Table 5 includes rewet data obtained during a test at Courtray Laboratories (ASH-R-2). Sample 1 is a diaper containing a pulpless core that was constructed so that the SAP was distributed to the outer edges of the core beyond the shadow of the transfer layer. Sample 2 was constructed in a manner similar to that shown in FIG. 7 and hence the SAP was contained within the lateral boundaries of the shadow of the transfer layer. The results reveal that Sample 2 had a lower rewet value. The reduction from 2186 mg to 1064 mg is a significant reduction in rewet value, thus indicating a significant improvement in dryness.

TABLE 5

Courtray Rewet Data

| (mg) | Back | Front | Total |
|---|---|---|---|
| Sample 1 | | | |
| Nr1 | 991 | 1039 | 2030 |
| Nr2 | 1045 | 1031 | 2076 |
| Nr3 | 1359 | 1090 | 2449 |
| Nr4 | 1112 | 1060 | 2186 |
| Average | 1127 | 1060 | 2186 |
| Sample 2 | | | |
| Nr1 | 567 | 511 | 1078 |
| Nr2 | 563 | 521 | 1084 |
| Nr3 | 507 | 513 | 1020 |
| Nr4 | 570 | 504 | 1074 |
| Average | 552 | 512 | 1064 |

Figure 8:
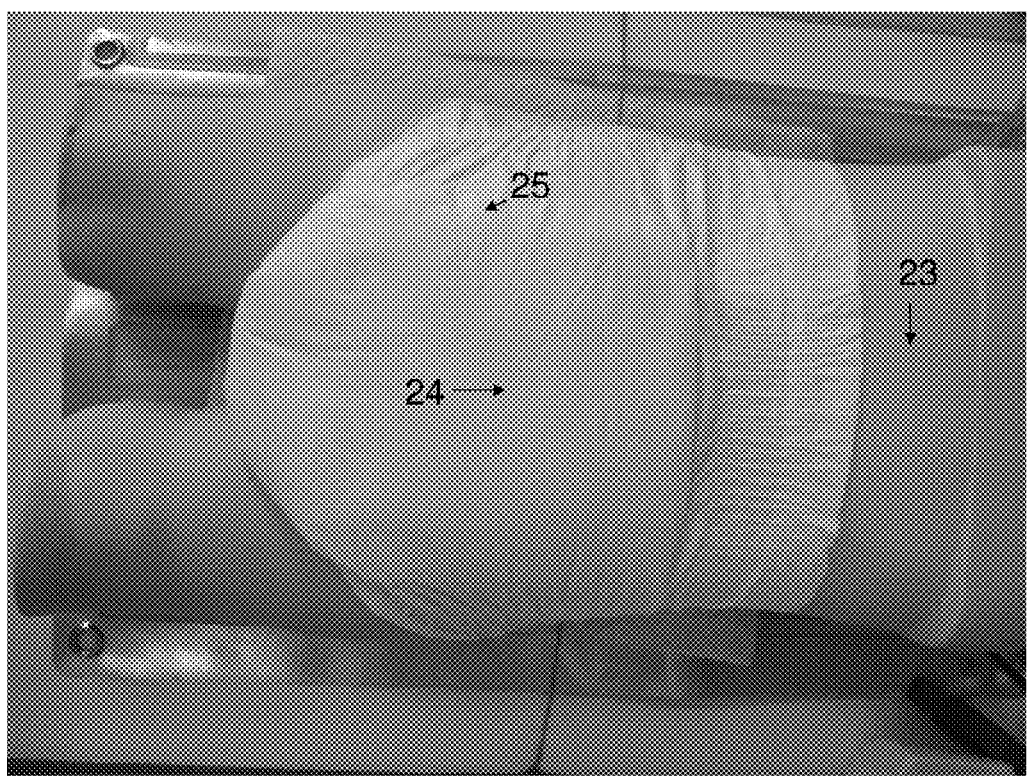
FIG. 8 is a picture of a test mannequin illustrating the concept of containing the SAP by gluing the tow adjacent to the SAP layer.

FIG. 8 is a photograph of a mannequin 23 from the Courtray Lab used in a rewet test. The mannequin 23 is diapered with a pulpless core diaper utilizing the gluing pattern illustrated in FIG. 7 similar to Sample 2 in the test discussed above. The diaper was insulted with colored 1% synthetic urine solution. The pulp core 24 is colored with the synthetic urine solution and shows where the synthetic urine in located in the diaper and hence, shows the SAP distribution. A sharp demarcation 25 can be seen between the absorbent core and the edge of the diaper showing that the SAP has been contained and has not shifted in the CD direction.

Other embodiments, uses, and advantages of the various preferred embodiments of invention described herein will be apparent to those skilled in the art from consideration of the specification and practice of the invention disclosed herein. The specification should be considered exemplary only, and the scope of the invention is accordingly intended to be limited only by the following claims.

What is claimed is:

1. An absorbent article comprising:
   a liquid pervious top layer;
   a liquid impervious back layer;
   a pulpless absorbent core positioned at least partially between the liquid pervious top layer and the liquid impervious back layer, the core comprising super absorbent polymer and synthetic filament tow fibers selected from the group consisting of polyolefins, rayon, polycarbonates, cellulose acetate, and mixtures thereof;
   a curb consisting of a portion of the liquid impervious back layer that lies between a bottom of the core and a bottom edge of at least one leg cuff and configured to be directly exposed to urine and bowel movements that leak from the pulpless absorbent core, wherein the distance from the bottom of the core to the top of the curb is the curb height, the curb height being at least 6 mm; and
   at least one leg cuff attached to and positioned adjacent the top of and extending away from the curb in a direction substantially orthogonal from the longitudinal plane of the absorbent article, wherein a proximal end of the leg cuff is attached to the inner surface of the curb at a lateral edge of the curb.

2. The absorbent article of claim 1, wherein the curb height is at least 10 mm.

3. The absorbent article of claim 1, wherein the curb height is at least 15 mm.

4. The absorbent article of claim 1, wherein the absorbent core is rectangularly shaped.

5. The absorbent article of claim 1, wherein the SAP absorbency efficiency in the absorbent core is greater than 95%.

6. The absorbent article of claim 5, wherein the SAP and synthetic fibers are glued in the absorbent core and the glue is applied using a slot coater.

7. The absorbent article of claim 5, further comprising a transfer layer, wherein the absorbent core is made by gluing an amount of SAP such that the width of the glued SAP is less than the width of the transfer layer.

8. The absorbent article of claim 6, further comprising a transfer layer, wherein the absorbent core is made by gluing an amount of SAP such that the width of the glued SAP is less than the width of the transfer layer.

9. The absorbent article of claim 1, wherein the SAP and synthetic fibers are glued in the absorbent core and the glue is applied using a slot coater.

10. The absorbent article of claim 1, further comprising a transfer layer, wherein the absorbent core is made by gluing an amount of SAP such that the width of the glued SAP is less than the width of the transfer layer.

11. An absorbent article comprising:
    a liquid pervious top layer;
    a liquid impervious back layer;
    a pulpless absorbent core positioned at least partially between the liquid pervious top layer and the liquid impervious back layer, the core comprising super absorbent polymer and synthetic filament tow fibers selected from the group consisting of polyolefins, rayon, polycarbonates, cellulose acetate, and mixtures thereof;
    a curb consisting of a portion of the liquid impervious back layer that is adjacent a bottom of the core and extends away from a longitudinal plane of the absorbent article on lateral sides of the absorbent core to a distal end of the curb, the curb creating a space between the portions extending away from a longitudinal plane on lateral sides of the absorbent core and configured to be directly exposed to urine and bowel movements that leak from the pulpless absorbent core; and
    at least one leg cuff attached to and positioned adjacent to and extending away from the distal end of the curb in a direction substantially orthogonal from the longitudinal plane of the absorbent article, wherein a proximal end of the leg cuff is attached to the inner surface of the curb at a lateral edge of the curb;
    wherein the space created by the curb forms a pool volume that is at least the same volume as the Centrifuge Retention Capacity (CRC) of the central 60% of the absorbent core.

12. The absorbent article of claim 11, wherein the pool volume is greater than 275 milliliters.

13. The absorbent article of claim 11, wherein the pool volume is greater than 300 milliliters.

14. The absorbent article of claim 11, wherein the pool volume is greater than 450 milliliters.

15. The absorbent article of claim 11, wherein the SAP absorbency efficiency in the absorbent core is greater than 95%.

16. The absorbent article of claim 15, wherein the SAP and synthetic fibers are glued in the absorbent core and the glue is applied using a slot coater.

17. The absorbent article of claim 15, further comprising a transfer layer, wherein the absorbent core is made by gluing an amount of SAP such that the width of the glued SAP is less than the width of the transfer layer.

18. The absorbent article of claim 16, further comprising a transfer layer, wherein the absorbent core is made by gluing an amount of SAP such that the width of the glued SAP is less than the width of the transfer layer.

19. The absorbent article of claim 11, wherein the SAP and synthetic fibers are glued in the absorbent core and the glue is applied using a slot coater.

20. The absorbent article of claim 11, further comprising a transfer layer, wherein the absorbent core is made by gluing an amount of SAP such that the width of the glued SAP is less than the width of the transfer layer.

21. The absorbent article of claim 11, wherein the absorbent core is rectangularly shaped.

* * * * *